United States Patent
Schultz (10) Patent No.: US 7,169,406 B2
(45) Date of Patent: Jan. 30, 2007

(54) GROWTH FACTOR DELIVERY SYSTEMS FOR THE HEALING OF WOUNDS AND THE PREVENTION OF INFLAMMATION AND DISEASE

(75) Inventor: Clyde L. Schultz, Ponte Vedra, FL (US)

(73) Assignee: DirectContact LLC, Nôrth Reading, MA (US)

( * ) Notice: Subject to any disclaimer, the term of this patent is extended or adjusted under 35 U.S.C. 154(b) by 32 days.

(21) Appl. No.: 10/340,434

(22) Filed: Jan. 10, 2003

(65) Prior Publication Data

US 2003/0203001 A1    Oct. 30, 2003

Related U.S. Application Data

(63) Continuation-in-part of application No. 10/132,843, filed on Apr. 25, 2002.

(51) Int. Cl.
  *A61K 9/00*  (2006.01)
  *A61F 13/00* (2006.01)

(52) U.S. Cl. .................. 424/429; 424/40; 424/422; 424/427; 424/484

(58) Field of Classification Search ............... 424/400, 424/422, 427, 429, 484
See application file for complete search history.

(56) References Cited

U.S. PATENT DOCUMENTS

| | | |
|---|---|---|
| 4,617,299 A | 10/1986 | Knepper |
| 4,668,506 A | 5/1987 | Bawa |
| 4,731,244 A | 3/1988 | Talle et al. |
| 4,923,467 A | 5/1990 | Thompson |
| 4,931,279 A | 6/1990 | Bawa et al. |
| 4,939,135 A | 7/1990 | Robertson et al. |
| 4,973,466 A | 11/1990 | Reich |
| 4,981,841 A | 1/1991 | Gibson |
| 4,983,580 A | 1/1991 | Gibson |
| 5,053,388 A | 10/1991 | Gibson et al. |
| 5,104,408 A | 4/1992 | Thompson |
| 5,124,155 A | 6/1992 | Reich |
| 5,124,392 A | 6/1992 | Robertson et al. |
| 5,156,622 A | 10/1992 | Thompson |
| 5,171,318 A | 12/1992 | Gibson et al. |
| 5,196,027 A | 3/1993 | Thompson et al. |
| 5,212,168 A | 5/1993 | Schwartz |
| 5,271,939 A | 12/1993 | Robertson et al. |
| 5,358,706 A | 10/1994 | Marlin et al. |
| 5,360,611 A | 11/1994 | Robertson et al. |
| 5,401,509 A | 3/1995 | Robertson et al. |
| 5,401,510 A | 3/1995 | Robertson et al. |
| 5,433,745 A | 7/1995 | Graham et al. |
| 5,472,703 A | 12/1995 | Vanderlaan et al. |
| 5,525,349 A | 6/1996 | Robertson et al. |
| 5,550,188 A | 8/1996 | Rhee et al. |
| 5,565,519 A | 10/1996 | Rhee et al. |
| 5,573,775 A | 11/1996 | Robertson et al. |
| 5,580,570 A | 12/1996 | Robertson et al. |
| 5,582,835 A | 12/1996 | Robertson et al. |
| 5,589,184 A | 12/1996 | Robertson et al. |
| 5,589,185 A | 12/1996 | Robertson et al. |
| 5,597,381 A | 1/1997 | Rizzo, III |
| 5,607,688 A * | 3/1997 | Cejkova et al. ............. 424/429 |
| 5,616,502 A | 4/1997 | Haugland et al. |
| 5,665,373 A | 9/1997 | Robertson et al. |
| 5,695,509 A * | 12/1997 | El Hage ..................... 606/166 |
| 5,723,131 A | 3/1998 | Schultz et al. |
| 5,767,079 A | 6/1998 | Glaser et al. |
| 5,811,446 A | 9/1998 | Thomas |
| 5,836,313 A | 11/1998 | Perez et al. |
| 5,932,205 A | 8/1999 | Wang et al. |
| 5,942,487 A | 8/1999 | Ogawa et al. |
| 5,973,089 A | 10/1999 | Meijs et al. |
| 6,063,116 A | 5/2000 | Kelleher |
| 6,124,273 A | 9/2000 | Drohan et al. |
| 6,143,315 A | 11/2000 | Wang et al. |
| 6,201,065 B1 | 3/2001 | Pathak et al. |
| 6,201,164 B1 | 3/2001 | Wulff et al. |
| 6,248,715 B1 | 6/2001 | Rosenberg et al. |
| 6,261,545 B1 | 7/2001 | Okamoto |
| 6,268,341 B1 | 7/2001 | Rosenberg et al. |

(Continued)

FOREIGN PATENT DOCUMENTS

EP    0 782 016 A2    7/1997

(Continued)

OTHER PUBLICATIONS

Hillman. "Management of acute glaucoma with pilocarpine-soaked hydrophilic lens" *Br. J. Ophthal.*, 58: 674-679 (1974).

(Continued)

*Primary Examiner*—Ruth A Davis
(74) *Attorney, Agent, or Firm*—Clark & Elbing LLP (57) ABSTRACT

The present invention features hydrogel drug delivery systems and methods of producing and using such systems for the treatment of wounds. The systems are based on a hydrogel into which a low concentration of growth factor, e.g., epidermal growth factor, is passively transferred from a dilute aqueous solution. When placed in contact with a wounded tissue, the growth factor passively transfers out of the contact lens to provide accelerated healing. The systems are applicable to ocular and other wound treatments.

20 Claims, 1 Drawing Sheet

U.S. PATENT DOCUMENTS

| | | |
|---|---|---|
| 6,331,309 B1 | 12/2001 | Jennings, Jr. et al. |
| 6,410,045 B1 | 6/2002 | Schultz et al. |
| 2001/0046518 A1 | 11/2001 | Sawhney |

FOREIGN PATENT DOCUMENTS

| | | |
|---|---|---|
| EP | 0 958 831 A1 | 11/1999 |

OTHER PUBLICATIONS

Wilson et al. "The Fas-Fas Ligand System and Other Modulators of Apoptosis in the Cornea" *Investigative Ophthalmology and Visual Sciences*, 37(8): 1582-92 (1996).

Lohmann et al. "Screening of Myopic Lasik Patients with Aggressive Woundhealing: Quantitative Determination of EGF mRNA in Corneal Epithelial Cells" 97th *Annual Meeting German Ophthalmological Society*, K180 Berling Sep. 23-26, 1999.

Dua and Azuara-Blanco, "Amniotic Membrane Transplantation," *Br. J. Ophthalmol.* 83(6):748-752 (1999).

Wang et al., "Reduction in Corneal Haze and Apoptosis by Amniotic Membrane Matrix in Excimer Laser Photoablation in Rabbits," *J. Catract Refract. Surg.* 27(2):310-319 (2001).

Woo et al., "Effects of Amniotic Membrane on Epithelial Wound Healing and Stromal Remodelliing After Excimer Laser Keratectomy in Rabbit Cornea," *Br. J. Ophthalmol.* 85(3):345-349 (2001).

European Search Report for EP03719865.

European Search Report for EP03719865, Aug. 4, 2005.

\* cited by examiner

GROWTH FACTOR DELIVERY SYSTEMS FOR THE HEALING OF WOUNDS AND THE PREVENTION OF INFLAMMATION AND DISEASE

CROSS-REFERENCE TO RELATED APPLICATIONS

This application is a continuation-in-part of U.S. application Ser. No. 10/132,843, filed Apr. 25, 2002, hereby incorporated by reference.

BACKGROUND OF THE INVENTION

In general, the invention relates to the fields of hydrogels, drug delivery systems, wound healing, and reduction of pain and inflammation.

Corneal wounds caused by injury, disease, or surgery represent a serious medical condition that may lead to loss of sight. For example, persistent epithelial defects can lead to stromal melting, which causes serious visual dysfunction. Wound healing of corneal mucosal tissue has taken on increased importance with the advent of laser corrective surgery to re-establish normal vision for people who do not wish to wear contact lenses or spectacles. These laser surgical methods are used to correct vision for nearsightedness (myopia), farsightedness (hyperopia), and astigmatism. The methods include laser in situ keratomileusis (LASIK), laser epithelial keratomileusis (LASEK), and photo-refractive keratectomy (PRK).

LASIK refers to the use of a laser to reshape the cornea without invading the adjacent cell layers. During the LASIK procedure a microkeratome is used to separate the surface layers of the cornea and create a corneal flap (160–180 microns deep). This flap stays attached to the rest of the cornea and is folded back on one side to expose the stroma of the cornea. The laser delivers pulses of ultraviolet light onto the inner cornea (stroma). Each pulse removes a microscopic layer of the inner cornea to reshape the surface of the cornea. For nearsighted patients, the procedure flattens the cornea. For farsighted patients, the procedure increases the curvature of the cornea. For astigmatism, selected tissues are removed at certain angles to make the cornea more spherical in shape. After exposure to the laser is completed, the corneal flap is replaced where it bonds without the need for stitches. The anterior layers of the cornea (epithelium, Bowman's Layer) are largely preserved. Once the surgery is completed, the eye is left to heal normally with the exception of eye drops, which are used to prevent infection & swelling, with varying degrees of success. Following the surgery, patients are able to see clearly without depending on glasses or contacts.

During PRK, the surgeon removes the epithelium (the anterior layer of the cornea or Bowman's Layer), which is a thin layer of protective skin that covers the cornea. This layer can be removed with an excimer laser or a brush. During the procedure, the patient stares at a fixation light. In less than a minute, the laser removes the proper amount of tissue while it reshapes the surface of the cornea. The excimer laser delivers pulses of ultraviolet light into the cornea. This exposure to laser radiation reduces or eliminates nearsightedness by flattening the central cornea and relocating the focal point of the lens onto the retina rather than in front of it, which produces sharper vision. Following surgery, a bandage contact lens is placed on the eye for 2–3 days. Because the epithelium was removed, patients may experience blurry vision for three to five days. Eye drops and the contact lens are effective in reducing postoperative discomfort. The purpose of the contact lens given to PRK patients post-surgically is to protect the leading edge of the corneal epithelium that is regenerating along the surface of the eye, post-surgery. As patients blink, the newer leading edge of the epithelium may be removed. As a result, recovery takes longer and there is an increased risk of infection.

LASEK is similar to PRK but the epithelium is detached by using an alcohol solution that weakens the epithelium and allows it to fold back into a flap. A laser is then used to re-shape the cornea and correct vision acuity.

All three procedures can result in corneal epithelial defects, and inflammation and infection may also occur. These complications can lead to acuity regression, pain, or other adverse effects. Corneal defects from injury or other types of surgery, such as corneal transplants, may also results in these undesirable outcomes. Wound healing is thus of critical importance for the outcome of surgery. There exists a need, therefore, for devices and treatments that promote healing of corneal wounds.

SUMMARY OF THE INVENTION

The present invention features hydrogel drug delivery systems and methods of producing and using such systems for the treatment of wounds. The systems are based on a hydrogel into which a growth factor, e.g., epidermal growth factor (EGF), is passively transferred from a dilute aqueous solution. When placed in contact with a wounded tissue, the growth factor passively transfers out of the hydrogel to provide accelerated healing and a concomitant reduction in pain. The amount of growth factor absorbed into the hydrogel may be $\leq 350$ ppb, but this amount surprisingly is effective in producing a therapeutic effect likely because the delivery system is localized and provides a sustained release of the factor. Higher concentrations of growth factor may also be employed. The systems are applicable to ocular wounds, especially after vision correcting surgery, as well as other wound treatments.

Accordingly, in one aspect, the invention features a polymeric hydrogel that contains a substantially pure growth factor. Exemplary growth factors include epidermal growth factor, platelet derived growth factor, hepatocytic growth factor, human growth hormone, fibroblast growth factor, and combinations thereof. The concentration of the growth factor is, for example, between 0.005 and 350 ppb. Other exemplary concentrations include at most 1, 10, 25, 50, or 100 ppm. The hydrogel has a water content of, for example, between 37.5% and 75% by weight. Exemplary hydrogel materials include a tetrapolymer of hydroxymethylmethacrylate, ethylene glycol, dimethylmethacrylate, and methacrylic acid. Other examples of hydrogels include etafilcon A, vifilcon A, lidofilcon A, vasurfilcon A, and polymacon B. In addition, variations of these polymers formed by the use of different packing solutions (e.g., phosphate-buffered saline and boric acid) in the manufacturing process are also included. The hydrogel may be ionic or non-ionic. In various embodiments, the growth factor is capable of being passively released into an environment, e.g., an ocular environment, under ambient or existing conditions. In other embodiments, the hydrogel may be shaped as a contact lens, e.g., one capable of correcting vision. Such a contact lens may be capable of correcting vision in the range of +8.0 to −8.0 diopters, including plano, and may have a base curve between 8.0 and 9.0. Hydrogels of the invention may further include other therapeutic compounds as described herein, e.g., an anti-inflammatory compound, such as dexamethasone, fluorometholone, rimexolone, or prednisolone.

In another aspect, the invention features a polymeric hydrogel including an anti-inflammatory compound. Exemplary polymers and anti-inflammatory compounds are as described above. The concentration of the anti-inflammatory compounds is, for example, between 0.001 and 100 ppm, e.g., at most 0.01, 0.1, 1, 10, 15, 20, 30, or 50 ppm.

The invention further features a method for making a hydrogel drug delivery system by placing the hydrogel, e.g., a contact lens, in an aqueous solution containing a substantially pure growth factor as described herein, which is passively transferred to the hydrogel. This method may further include the steps of washing the hydrogel in an isotonic saline solution and partially desiccating the hydrogel prior to placement in the solution. The aqueous solution has, e.g., a pH between 6.9 and 7.4 and between 0.01 and 10 ng growth factor per µL. The concentration of growth factor in the hydrogel after soaking (i.e., after the medicated hydrogel is manufactured) is, for example, between 5 and 350 ppb. In one embodiment, the hydrogel is placed in the solution of growth factor for at least 30 minutes. The aqueous solution may further include another therapeutic compound as described herein, e.g., an anti-inflammatory compound, such as dexamethasone, fluorometholone, rimexolone, or prednisolone. Hydrogels containing these other therapeutic compounds may also be obtained by omitting the growth factor in the soaking solution.

In another aspect, the invention features a method for treating a wound. The method includes placing a hydrogel, as described herein, in contact with the wound, wherein the growth factor or anti-inflammatory compound or both are passively released from the hydrogel to treat the wound. In one embodiment, the hydrogel further acts as a protective shield against mechanical abuse. In various embodiments, the wound is in endothelial tissue, epithelial tissue, the lung, the skin, or the digestive tract. The hydrogel may be placed in a body cavity. In another embodiment, the method causes a reduction in pain compared to a wound not contacted with the medicated hydrogel. The hydrogel may passively release, for example, at least 0.01, 0.05, 0.1, 0.5, 1, 10, 15, or 20 µg of a growth factor, and the hydrogel may be placed in contact with the wound for at least 0.5, 1, 1.5, 2, 2.5, 3, 3.5, 4, 4.5, 5, 7.5, 10, 15, or 24 hours. The hydrogel may also passively release at least 0.01, 0.05, 0.1, 0.5, 1, 10, 15, 20, 50, 100, or 1000 µg of other compounds, as described herein.

The invention also features a method of delivering a growth factor including the steps of placing a polymeric hydrogel of the invention in contact with a wound that is in contact with a replenishable bodily fluid; and allowing the growth factor to release passively from the hydrogel into the replenishable bodily fluid. In this method, the release of the growth factor from the hydrogel into the replenisbable bodily fluid is accelerated compared to the release of the growth factor from the hydrogel into a non-replenishable bodily fluid. An exemplary wound is an ocular wound, and an exemplary replenishable bodily fluid is tear fluid. This method may also be used to deliver anti-inflammatory or other compounds as described herein.

As used herein, by "ambient conditions" is meant room temperature and pressure.

By "existing conditions" is meant in situ, as in the eye or other body system.

By "substantially pure" is meant having a purity of greater than 75% by weight. A growth factor of the invention is, for example, greater than 85%, 90%, 95%, or even 99% pure. Use of the term is intended to define purity from other biological compounds, e.g., proteins, carbohydrates, and lipids that are commonly associated with the growth factor in vivo.

By "treating" is meant the medical management of a patient with the intent that a prevention, cure, stabilization, or amelioration of the symptoms will result. This term includes active treatment, that is, treatment directed specifically toward improvement of the disorder; palliative treatment, that is, treatment designed for the relief of symptoms rather than the curing of the disorder; preventive treatment, that is, treatment directed to prevention of the disorder; and supportive treatment, that is, treatment employed to supplement another specific therapy directed toward the improvement of the disorder. The term "treatment" also includes symptomatic treatment, that is, treatment directed toward constitutional symptoms of the disorder. The term further includes the promotion of wound closure or healing.

By "therapeutically effective amount" is meant an amount of a compound sufficient to produce a preventative, healing, curative, stabilizing, or ameliorative effect in the treatment of a condition, e.g., an eye wound.

By "wound" is meant an injury to any tissue. Examples of wounds include burns, lacerations, abrasions, bites, surgical wounds, puncture wounds, and ulcers.

By "ocular environment" is meant the tissues of and surrounding the eye, including, for example, the sclera, cornea, and other tissues of the ocular cavity.

By "replenishable bodily fluid" is meant a fluid produced by a mammal that is periodically replaced with new fluid. Examples of replenishable bodily fluids include tears, saliva, mucous, gastric fluids, and urine.

All percentages described in the present invention are by weight unless otherwise specified.

Other features and advantages of the invention will apparent from the following description and the claims.

DETAILED DESCRIPTION OF THE INVENTION

This invention provides a polymeric drug delivery system including a hydrogel containing a growth factor, e.g., EGF. Allowing passive transference of the growth factor from a dilute aqueous solution into the hydrogel produces the delivery system. The hydrogel, when placed in contact with a wound, delivers a low concentration of the growth factor. The delivery of the growth factor is sustained over an extended period of time, which is of particular utility in environments, e.g., the eye, that are periodically flushed with bodily fluids, e.g., tears. This sustained delivery accelerates the wound healing process while avoiding potential damaging effects of localized delivery of high concentrations of compounds, e.g., from eye drops.

Drug Delivery System

Hydrogels. This invention may employ different polymer compositions that are useful in the treatment of a variety of tissues. For example, in the ocular environment, conventional soft contact lenses can be used and can be either ionic or non-ionic hydrogels containing between 37.5%–75% water by weight and can have any base curve, e.g., from 8.0 to 9.0. The contact lenses may also have the ability to correct vision, for example, over a range of diopters of +8.0 to −8.0, including plano. Exemplary hydrogel contact lens materials include etafilcon A, vifilcon A, lidofilcon A, polymacon B, vasurfilcon A, and a tetrapolymer of hydroxymethylmethacrylate, ethylene glycol, dimethylmethacrylate, and methacrylic acid. These materials may also be employed, in other physical forms, in treating wounds in other tissues. Other suitable hydrogel materials are known to those skilled in the art. The hydrogels may be insoluble or may dissolve over time in vivo, e.g., over one day or one week. The growth factor is passively delivered, for example, by diffusion out of the hydrogel, by desorption from the hydrogel, or by release as the hydrogel dissolves.

The drug delivery system may be produced from a partially desiccated hydrogel (or equivalently a partially hydrated hydrogel). The desiccation step removes, for example, approximately 5%, 10%, 15%, 20%, 25%, 30%, 40%, 50%, 60%, or 75% of the water in a hydrogel. Desiccation can occur, for example, by exposure of the hydrogel to ambient or humidity controlled air, by heating the hydrogel for a specific period of time, or by blowing dried gas, such as $N_2$, over the hydrogel. In one embodiment, the hydrogel is saturated with physiological (isotonic) saline prior to desiccation. The partially desiccated hydrogel is then soaked, e.g., for at least 30 minutes, in a dilute aqueous solution of growth factor, e.g., at a pH between 6.9 to 7.4. The hydrogels may also be soaked for at least 1 hour, 6 hours, 12 hours, or 24 hours. The concentration of growth factor into which the hydrogel is placed is typically 10 ng/μL or less, e.g., at most 5 ng/μL, 1 ng/μL, 0.1 ng/μL, or 0.01 ng/μL. Higher concentrations may also be used, for example, to reduce the soaking time. The growth factor is passively transferred into the hydrogel. This transfer may occur at least in part by rehydrating the hydrogel. Diffusion of the growth factor into the water in the hydrogel may also occur. In alternative embodiments, a fully hydrated or fully desiccated hydrogel is placed in the soaking solution to produce the medicated hydrogel.

Desirably, the concentration of growth factor transferred to the hydrogel is substantially lower than the solution in which the hydrogel is soaked. For example, the concentration of growth factor in the hydrogel is at least 2×, 5×, or 10× less than that of the soaking solution. Some growth factors, however, may have a higher affinity for a hydrogel than aqueous solution, and such a hydrogel will have a higher concentration of growth factor than the solution in which it was soaked. The water content and type of hydrogel, time and conditions, e.g., temperature of soaking, composition of the soaking solution (e.g., ionic strength and pH), and type of growth factor employed also may influence the concentration of growth factor in the drug delivery system. Since the water content of the hydrogel also helps to determine the total amount of growth factor present in a hydrogel; it represents a variable by which to control the amount of growth factor delivered to a tissue. The production of a hydrogel containing a specified amount of growth factor can be accomplished by routine experimentation by one skilled in the art. Exemplary hydrogels include between 5 and 350 ppb of growth factor, for example, between 5 and 250 ppb, 5 and 100 ppb, 5 and 50 ppb, or 5 and 10 ppb. The concentration of growth factor in the hydrogel may, however, be higher, e.g., at most 100, 75, 50, 25, 10, or 1 ppm.

Growth factors. Growth factors are a heterogeneous group of proteins capable of stimulating growth and the multiplication of cells. Exemplary growth factors include epidermal growth factor, platelet derived growth factor, hepatocytic growth factor, human growth hormone, fibroblast growth factor, and combinations thereof. These growth factors may be natural, synthetic, or recombinant growth factors or growth factor derivatives from any animal, for example, humans, or any domesticated animal or pet species. Such growth factors also include biologically active growth factors and analogs. Peptide growth factors play important biological roles by regulating many of the processes involved in normal wound healing including migration, mitosis, and differentiation of cells. Growth factors are commercially available or may be isolated using methods known in the art.

Other compounds. The hydrogels of the invention may also contain medicaments other than growth factors. These additional compounds include, without limitation, analgesics, anti-inflammatory drugs (e.g., dexamethasone, fluorometholone, rimexolone and prednisolone), antibodies, meganins, self-proteins, pharmaceutical drugs, and antibiotic compounds. These other compounds may also be used at reduced concentrations from their typically prescribed dosages. For example, these chemicals may be delivered in concentrations of less than 100, 50, 25, 10, 1, 0.1, 0.01, or 0.001 ppm at various sites (e.g., the eye) and under different conditions (e.g. ambient or existing).

The use of preservatives is non-ideal as they may transfer to a hydrogel at a disproportionately high concentration and cause cytotoxicity.

Treatment. To treat a wound, a drug delivery system of the invention may be placed in contact with a damaged tissue. When the system is shaped as a contact lens, the lens may simply be placed in the eye normally in order to deliver the growth factor. In order to effect accelerated healing of other wounds, the hydrogel may be part of a bandage or may be adhered (e.g., by adhesives or sutures) to the wounded tissue. If the hydrogel is placed internally in a patient, the hydrogel is advantageously biodegradable.

Hydrogels may be considered to be disposable and may be replaced after a specified period of time, e.g., at least 0.5, 1, 1.5, 2, 2.5, 3, 3.5, 4, 4.5, 5, 7.5, 10, 15, or 24 hours. Alternatively, a hydrogel that has a depleted amount of growth factor may be recycled by desiccating and soaking the hydrogel again.

Treatment Approaches

The invention may be used in conjunction with healing many types of wounds, including, without limitation, ocular, oral, lung, digestive tract, skin, large intestine, small intestine, colon, and other wounds to endothelial, mucosal, or epithelial tissues. As stated above, the invention provides accelerated healing by delivering a growth factor to an injured tissue. In certain embodiments, at least 0.01, 0.05, 0.1, 0.5, 1, 5, 10, 15, or 20 μg of the growth factor is released from the hydrogel. This delivery occurs by passive transfer and allows medications to be released into fluids of the body, e.g., ocular fluid. The growth factor stimulates proliferation of cells surrounding a wound to close the wound and replace damaged cells. Because the growth factor is localized by the hydrogel, which provides greater control over release of the growth factor or drug, a lesser amount of growth factor may in many cases be needed to effect wound healing than if, e.g., topical solutions, such as eye drops are used. Accelerated healing may also reduce the pain and inflammation associated with a particular wound and may help prevent infection. In addition, the hydrogel may also act as a physical barrier to provide protection from mechanical abuse and to prevent adherence of the healing tissue to adjacent tissues. The use of hydrogels of the invention may also allow patients to be treated using fewer applications than with traditional methods. For example, a patient treated using the hydrogels of the invention may be able to treated only once in a period of at least 48 hours.

In desirable embodiments, a hydrogel of the invention is used to treat a wound that is in contact with a replenisbable bodily fluid, e.g., tears. In these embodiments, the growth factor is released from the hydrogel at a more rapid rate than the release of the growth factor into a fixed volume of fluid because as the bodily fluid is replenished, the growth factor released is flushed away from the site of application causing an increase in the relative rate of diffusion of the growth factor out of the hydrogel. The replenishing action of fluids such as tears may also effectively increase the rate of diffusion of the growth factor into the fluid and lead to earlier onset of therapeutic activity. For medicated hydrogels of the invention placed in contact with a non-replenishable bodily fluid (i.e., one where replacement is very slow or nonexistent on the time-scale of drug release), lower concentrations of a drug may be used since the drug is not flushed from the site as quickly as in a replenishable fluid.

Ocular Wounds. In one embodiment, the wound is an ocular wound, e.g., in corneal epithelial, endothelial, or retinal tissue. The invention is of particular utility after vision correcting surgery, such as LASIK, PRK, or LASEK. Soft and collagen contact lenses may be utilized to minimize post-surgical epithelial trauma and provide a stable healing environment. PRK typically requires a therapeutic contact lens for 3–4 days, and post-operative therapeutic drops are often prescribed. In the present invention, the hydrogel may be shaped as a contact lens that acts as a reservoir for the growth factor and can serve to protect the leading edge of wound healing from normal mechanical abuse. The growth factor gradually delivered in a low concentration from the hydrogel obviates the need for therapeutic drops. Therapeutic drops often include high concentrations of drugs because the majority of the drop is excreted from the eye in a short period of time. These high concentrations can cause additional damage to a wound, which is avoided by the use of the present, localized time-release drug delivery system.

A further understanding of the invention may be obtained from the following non-limiting examples.

EXAMPLE 1

Production of a Drug Delivery System

An exemplary drug delivery system was prepared as follows. Contact lenses were removed from their package and rinsed with saline to remove contact lens packing solution. The hydrogel lens materials were allowed to desiccate for 10–30 seconds. The hydrogel lens materials were placed into physiological saline that contained epidermal growth factor (EGF) at concentrations of 10 ng/µl or 5.0 ng/µl for at least 30 minutes. Lower concentrations may also be used. Longer passive transference times may also be used. Untreated or control lenses were placed in physiological saline without EGF.

EXAMPLE 2

Healing of Ocular Tissue

Ocular cells were placed into a sterile plastic dish. This dish contained a 5-mm disk. The purpose of the disk was to prevent cells from growing in the covered area. When the disk was removed, a 5-mm "wound" or "hole" was present. Contact lenses were then added to these cell sheets with the wounds. The lenses were left in contact with the cell sheets for a minimum of 30 minutes. Minimal medium was used to maintain the cell cultures. Cells were incubated at 35° C.±2° C. in 5% $CO_2$. Contact lenses with or without EGF were produced as in Example 1. The contact lenses used were polymacon B, vifilcon A, and lidofilcon A hydrogel polymers.

The cell sheets were then viewed over time, and the diameter of the hole was measured.

The results are expressed in terms of closure of the in vitro wound over time.

Epithelial Cells and Tissue. Epithelial (rabbit corneal epithelial cells) cells were seeded on a dish and contacted with control and EGF-containing contact lenses. At 48 hours there was a 25% difference in the closure rate between the EGF-treated cells and the non-EGF treated cells. At 72 hours, there was a 43% difference in the closure rate between the EGF-treated epithelial tissue and the controls. The hydrogel material that was used was vifilcon A, an ionic polymer with a water content of 55%. The polymer had been incubated with 10 ng/µL EGF for one hour at 4° C. prior to use in the experiments.

Closure rates were calculated by direct measurement of the diameter of the wound. Measurements were taken daily.

In a related series of experiments, a vifilcon A lens was incubated under the same conditions as above with 5.0 ng/µL of EGF and then contacted with an epithelial "wound" as above. At 48 hours, there was a 21% closure rate difference between controls and EGF treated hydrogel materials. At 72 hours, there was also a 21% difference in the closure rate. These results indicated that over a 72-hour period, the relative healing rates remained essentially the same for the treated and non-treated epithelial tissue, with the epithelial tissue treated with EGF always having an accelerated rate of healing.

The rate of wound healing increased with increased exposure of the hydrogel material to the wound. Further, compared to a wound not contacted with any lens, at 48 hours there was a 31% difference in the healing rates. Healing for tissue exposed to a lens soaked in 10 ng/µL of EGF increased from 14% at 48 hours to 25% at 72 hours.

Endothelial Cells and Tissue. Wounds caused in endothelial tissue (bovine corneal endothelial cells) were also healed by release of EGF from a vifilcon A lens. The lens, soaked in 10 ng/µL of EGF as above, showed a 73% difference in healing rates at 48 hours compared to a control. At 72 hours, the EGF-treated tissue had completely healed. In the control group, less than half (43%) of the tissue had healed. The same lens material exposed to 5 ng/µL of EGF showed a 31% difference in closure rate at 48 hours between the EGF treated group and the controls. At 72 hours, 53% of the tissue had healed in the EGF treated group, compared to 43% in the control.

Lidofilcon A hydrogel (non-ionic, water content=70%) materials were evaluated for their ability to deliver EGF to endothelial tissue to close wounds. The concentration of EGF used in the soaking solution was 10 ng/µL. At 48 hours, the EGF treated tissue showed a 54% increase in the healing rate (wound closure rate) as compared to controls. At 72 hours, there was a difference of 44%.

A third material, polymacon B, that is non-ionic and has a water content of 38%, was also evaluated for the ability to deliver EGF to wounds. The lenses were prepared using a soaking solution of 10 ng/µL of EGF. At 48 hours, the wound was 60% closed in the treated group and 27% closed in the non-treated group. At 72 hours, the difference in closure between the treated and untreated groups was 62%. In the EGF treated group at 72 hours, the wound had closed by 80%, while in the untreated group, the wound had closed by 46.8%.

EXAMPLE 3

Uptake and Release of EGF

Figure 1:
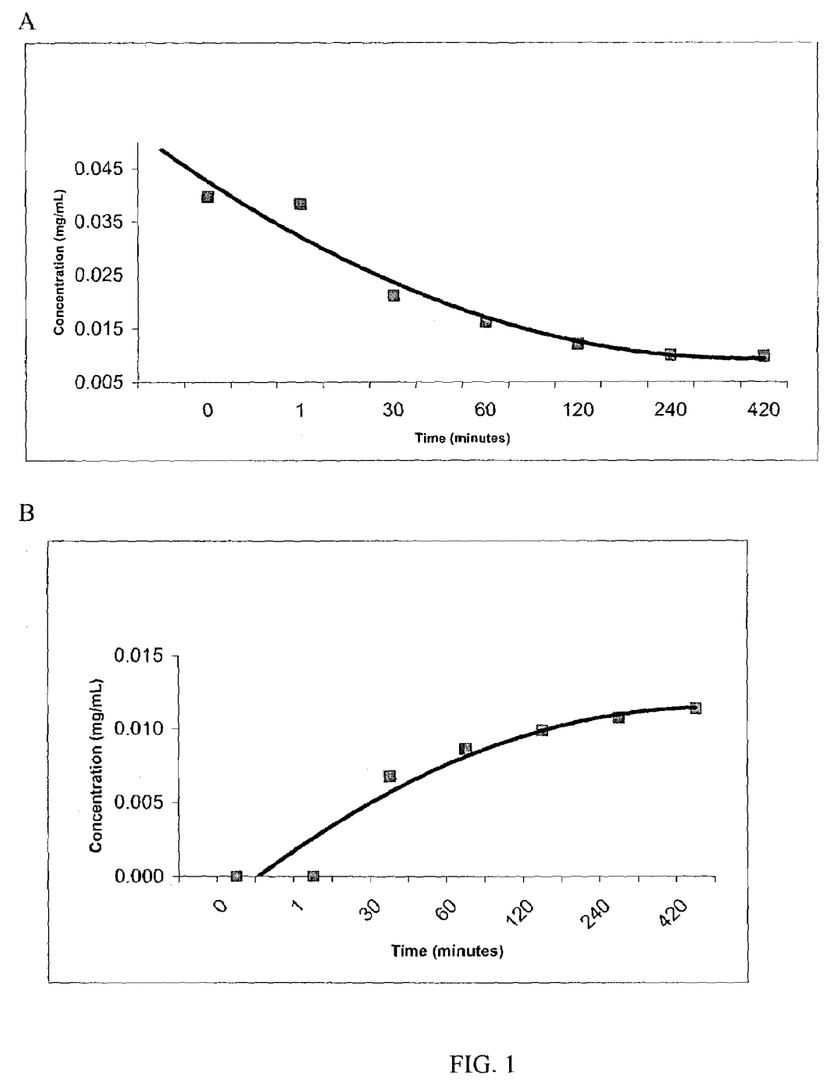
FIGS. 1A and 1B are groups of the uptake (A) and release (B) of EGF from vasurfilcon A contact lenses.

The amount of uptake and release of EGF from a contact lens depends on the water content or composition of the lens or both. Data were collected on the uptake and release of EGF from two types of lenses, lotrafilcon A (24% water) and vasurfilcon A (74% water). Both of these lenses are non-ionic. For uptake studies, thirty lenses of each type were placed in 25 mL of a solution containing 40 ppm of EGF. For release studies, the lenses produced by the uptake study were placed in 25 mL of solution not containing EGF after desiccation for 10–30 seconds. For both types of study, the amount of EGF in the solution was then measured at defined time intervals. For vasurfilcon A, about 75% of the EGF in solution was taken up by the lenses after 6 hours (FIG. 1A), at which point the lenses appeared to be in equilibrium with the solution, and about 37% of the EGF taken up was released after 7 hours (FIG. 1B), at which point the lenses appeared to be at or near equilibrium. The release data indicate that contact lenses can deliver a sustained dosage of EGF over a period of time. For lotrafilcon A, surprisingly, no measurable amount of EGF was taken up or released by the lenses. Based on a purely diffusional theory of uptake, at least some growth factor would have been expected to be taken up in the water in the lotrafilcon A contact lens. Two possible explanations for the differential uptake of EGF by the two polymers studied are 1) a water content higher than 24% is needed for uptake of EGF and 2) the lotrafilcon A polymer is chemically (thermodynamically) or structurally (kinetically) unfavorable for the entry of EGF.

EXAMPLE 4

Animal Tests

Contact lenses containing EGF, EGF and dexamethasone (an anti-inflammatory steroid), and human growth hormone (HGH) were tested in a rabbit model for efficacy and toxicity. New Zealand white rabbits were anesthetized, and then both eyes were abraded with a needle. A control contact lens was placed in the left eye, and a medicated contact lens was placed in the right eye of each rabbit for up to 4 hours prior to euthanasia. Control contact lenses (etafilcon A, an ionic lens with 58% water content) were washed with phosphate-buffered saline (PBS) prior to insertion. Medicated contact lenses (etafilcon A) were prepared by briefly drying the lens and then soaking it in 400 ppb, 4 ppm, or 10 ppm EGF or 400 ppb HGH in PBS for 24 hours. In another experiment, lenses were soaked in 200 ppb EGF and 12.5 ppm dexamethasone for 25 hours. No toxicity was observed in the rabbits at any concentration of EGF tested. Rabbits were visually scored on a 0–4 scale (0 being the best and 4 being the worst) for corneal edema (which is a measure of wound healing), inflammation, and exudate production.

EGF (lenses soaked in 400 ppb EGF) released from hydrogel contact lenses (right eye) healed wounds at an accelerated rate when compared to control eyes (left eye) for the first two hours after treatment. Data from four rabbits are shown in Table 1.

In another experiment, in addition to being abraded, the rabbits eyes were treated with a solution of lipopolysaccharide from *E. coli* O111:B4 (1 mg/mL) to induce inflammation. Lenses soaked in 200 ppb EGF and 12.5 ppm (see above) dexamethasone controlled inflammation and caused increased wound healing (right eye) compared to control eyes (left eye). EGF controlled healing of wounds even if there was an increase in inflammation.

Rabbit eyes (right eye) treated with HGH released from a contact lens (400 ppb soak) had increased wound healing and reduction in inflammation compared to control eyes (left eye) in rabbits. In addition, no toxicity was observed to the ocular tissue.

TABLE 1

Wound healing with contact lenses containing EGF

| Time (hours) | Corneal Edema Left | Corneal Edema Right | Inflammation Left | Inflammation Right | Exudate Left | Exudate Right |
|---|---|---|---|---|---|---|
| Rabbit 1 | | | | | | |
| 1 | 1 | 1 | 0 | 0 | 0 | 0 |
| 1.5 | 2 | 1 | 1 | 0 | 0 | 0 |
| 2 | 2 | 1 | 2 | 0 | 1 | 0 |
| 2.5 | 2 | 2 | 1 | 1 | 2 | 1 |
| 3 | 2 | 2 | 1 | 1 | 2 | 2 |
| 3.5* | 2 | 2 | 2 | 2 | 3 | 2 |
| Rabbit 2 | | | | | | |
| 1 | 1 | 1 | 1 | 0 | 0 | 0 |
| 1.5 | 1 | 1 | 0 | 0 | 0 | 0 |
| 2 | 2 | 2 | 1 | 1 | 2 | 2 |
| 2.5 | 2 | 2 | 1 | 1 | 1 | 3 |
| 3 | 2 | 1 | 1 | 2 | 2 | 2 |
| 3.5* | 2 | 2 | 1 | 2 | 1 | 2 |
| Rabbit 3 | | | | | | |
| 1 | 1 | 1 | 0 | 0 | 0 | 0 |
| 1.5 | 1 | 0 | 0 | 0 | 1 | 0 |
| 2* | 1 | 0 | 0 | 0 | 0 | 0 |
| Rabbit 4 | | | | | | |
| 1 | 1 | 0 | 0 | 0 | 0 | 0 |
| 1.5 | 1 | 0 | 0 | 0 | 0 | 0 |
| 2 | 1 | 1 | 0 | 0 | 0 | 1 |
| 2.5 | 1 | 1 | 0 | 0 | 0 | 0 |
| 3 | 1 | 1 | 0 | 0 | 0 | 0 |
| 3.5 | 1 | 1 | 0 | 0 | 0 | 0 |
| 4* | 1 | 1 | 0 | 0 | 0 | 0 |

*death of the rabbit

TABLE 2

Wound healing and treatment of inflammation with contact lenses containing EGF and dexamethasone

| Time (hours) | Corneal Edema Left | Corneal Edema Right | Inflammation Left | Inflammation Right | Exudate Left | Exudate Right |
|---|---|---|---|---|---|---|
| Rabbit 1 | | | | | | |
| 1 | 1 | 1 | 1 | 0 | 0 | 0 |
| 1.5 | 1 | 1 | 1 | 0 | 0 | 0 |
| 2 | 1 | 0 | 2 | 0 | 0 | 0 |
| 2.5 | 2 | 0 | 2 | 0 | 0 | 0 |
| 3 | 2 | 0 | 2 | 0 | 0 | 0 |
| 3.5* | 2 | 0 | 1 | 1 | 1 | 1 |
| Rabbit 2 | | | | | | |
| 1 | 1 | 1 | 1 | 0 | 0 | 0 |
| 1.5 | 2 | 1 | 2 | 0 | 0 | 0 |
| 2 | 2 | 1 | 2 | 0 | 0 | 0 |
| 2.5 | 2 | 1 | 2 | 1 | 1 | 0 |
| 3 | 2 | 1 | 2 | 0 | 2 | 0 |
| 3.5 | 2 | 1 | 2 | 1 | 1 | 1 |

TABLE 2-continued

Wound healing and treatment of inflammation with contact lenses containing EGF and dexamethasone

| Time | Corneal Edema | | Inflammation | | Exudate | |
|---|---|---|---|---|---|---|
| (hours) | Left | Right | Left | Right | Left | Right |
| 4.0* | 2 | 1 | 2 | 2 | 2 | 2 |
| Rabbit 3 | | | | | | |
| 1 | 1 | 1 | 1 | 0 | 0 | 0 |
| 1.5 | 1 | 1 | 1 | 0 | 0 | 0 |
| 2 | 1 | 1 | 2 | 0 | 1 | 0 |
| 2.5 | 1 | 1 | 1 | 0 | 0 | 0 |
| 3.0* | 1 | 0 | 1 | 0 | 0 | 0 |
| Rabbit 4 | | | | | | |
| 1 | 1 | 1 | 1 | 0 | 0 | 0 |
| 1.5 | 1 | 1 | 1 | 0 | 0 | 0 |
| 2 | 1 | 1 | 1 | 0 | 0 | 0 |
| 2.5 | 1 | 1 | 1 | 0 | 1 | 0 |
| 3 | 1 | 1 | 1 | 0 | 2 | 0 |
| 3.5 | 1 | 1 | 0 | 0 | 0 | 0 |
| 4* | 1 | 1 | 1 | 0 | 0 | 0 |

*death of the rabbit

TABLE 3

Wound healing with contact lenses containing HGH

| Time | Corneal Edema | | Inflammation | | Exudate | |
|---|---|---|---|---|---|---|
| (hours) | Left | Right | Left | Right | Left | Right |
| Rabbit 1 | | | | | | |
| 1 | 1 | 1 | 0 | 0 | 0 | 0 |
| 1.5 | 2 | 0 | 0 | 0 | 0 | 0 |
| 2 | 2 | 0 | 1 | 0 | 0 | 0 |
| 2.5 | 2 | 0 | 1 | 0 | 0 | 0 |
| 3 | 2 | 0 | 1 | 1 | 0 | 0 |
| 3.5* | 1 | 0 | 1 | 1 | 0 | 0 |
| Rabbit 2 | | | | | | |
| 1 | 1 | 1 | 0 | 0 | 0 | 0 |
| 1.5 | 1 | 1 | 0 | 0 | 0 | 0 |
| 2 | 1 | 1 | 1 | 0 | 0 | 0 |
| 2.5 | 1 | 0 | 1 | 0 | 0 | 0 |
| 3 | 1 | 0 | 1 | 0 | 0 | 0 |
| 3.5* | 1 | 0 | 0 | 0 | 0 | 1 |
| Rabbit 3 | | | | | | |
| 1 | 1 | 1 | 0 | 0 | 0 | 0 |
| 1.5 | 1 | 0 | 0 | 0 | 0 | 0 |
| 2 | 1 | 0 | 1 | 0 | 0 | 0 |
| 2.5 | 1 | 0 | 1 | 0 | 0 | 0 |
| 3.0 | 1 | 1 | 1 | 0 | 1 | 0 |
| 3.5* | 1 | 1 | 1 | 1 | 0 | 0 |
| Rabbit 4 | | | | | | |
| 1 | 1 | 1 | 0 | 0 | 0 | 0 |
| 1.5 | 1 | 1 | 0 | 0 | 0 | 0 |
| 2 | 1 | 0 | 1 | 0 | 0 | 1 |
| 2.5 | 1 | 1 | 1 | 0 | 0 | 1 |
| 3 | 1 | 1 | 1 | 0 | 0 | 1 |
| 3.5* | 1 | 1 | 0 | 1 | 0 | 1 |

*death of the rabbit

EXAMPLE 5

Human Testing

A polymacon B lens having 38% water content was soaked in 400 ppb EGF for 24 hours. This lens was placed in a human patient suffering from a recurring epithelial defect that was not responsive to traditional medical treatments. Clinical efficacy (i.e., wound healing) was observed after treatment with the medicated lens of the invention. Desirably treatment lasts for at least one hour. This type of injury is normally treated by the repeated introduction of eye drops, sometimes as often as every 4–5 minutes. A contact lens of the present invention, however, was able to produce a positive result with only one administration.

OTHER EMBODIMENTS

Modifications and variations of the described methods of the invention will be apparent to those skilled in the art without departing from the scope and spirit of the invention. Although the invention has been described in connection with specific desirable embodiments, it should be understood that the invention as claimed should not be unduly limited to such specific embodiments. Indeed, various modifications of the described modes for carrying out the invention, which are obvious to those skilled in the art, are intended to be within the scope of the invention.

All publications, patents, and patent applications mentioned in this specification are herein incorporated by reference to the same extent as if each individual publication, patent, or patent application was specifically and individually to be incorporated by reference.

Other embodiments are within the claims.

What is claimed is:

1. A polymeric hydrogel contact lens having a water content of between 37.5% and 75% comprising an anti-inflammatory compound, wherein said anti-inflammatory compound is present at a concentration of between 0.001 and 100 ppm.

2. The polymeric hydrogel of claim 1, wherein said anti-inflammatory compound is dexamethasone, fluorometholone, rimexolone, or prednisolone.

3. The polymeric hydrogel of claim 1, wherein said hydrogel is capable of producing a therapeutic effect after vision correcting surgery.

4. The polymeric hydrogel of claim 1, further comprising a growth factor.

5. The polymeric hydrogel of claim 4, wherein said growth factor is substantially pure.

6. The polymeric hydrogel of claim 4, wherein said growth factor is present at a concentration of between 5 and 350 ppb.

7. The polymeric hydrogel claim 4, wherein said growth factor is selected from the group consisting of epidermal growth factor, platelet derived growth factor, hepatocytic growth factor, human growth hormone, fibroblast growth factor, and combinations thereof.

8. The polymeric hydrogel of claim 7, wherein said growth factor is epidermal growth factor or human growth hormone.

9. The polymeric hydrogel of claim 4, wherein said growth factor is capable of being passively released into an environment under ambient conditions.

10. The polymeric hydrogel of claim 9, wherein said environment is an ocular environment.

11. The polymeric hydrogel of claim 4, wherein said growth factor is capable of being passively released into an environment under existing conditions.

12. The polymeric hydrogel of claim 11, wherein said environment is an ocular environment.

13. The polymeric hydrogel of claim 1, wherein said hydrogel comprises a tetrapolymer of hydroxmethylmethacrylate, ethylene glycol, dimethylmethacrylate, and methacrylic acid.

14. The polymeric hydrogel of claim 1, wherein said hydrogel is a plano contact lens.

15. The polymeric hydrogel of claim 1, wherein said hydrogel is capable of correcting vision.

16. The polymeric hydrogel of claim 15, wherein said hydrogel is capable of correcting vision in the range of +8.0 to −8.0 diopters.

17. The polymeric hydrogel of claim 15, said hydrogel having a base curve between 8.0 and 9.0.

18. The polymeric hydrogel of claim 1, wherein said hydrogel comprises an ionic polymer.

19. The polymeric hydrogel of claim 1, wherein said hydrogel comprises a non-ionic polymer.

20. The polymeric hydrogel of claim 1, wherein said hydrogel comprises etafilcon A, vifilcon A, polymacon B, lidofilcon A, or vasurfilcon A.

* * * * *

UNITED STATES PATENT AND TRADEMARK OFFICE
CERTIFICATE OF CORRECTION

| | |
|---|---|
| PATENT NO. | : 7,169,406 B2 |
| APPLICATION NO. | : 10/340434 |
| DATED | : January 30, 2007 |
| INVENTOR(S) | : Clyde L. Schultz |

It is certified that error appears in the above-identified patent and that said Letters Patent is hereby corrected as shown below:

Column 4, Line 34, replace "invention will apparent" with --invention will be apparent--.

Column 7, Line 1, replace "be able to treated" with --be able to be treated--.

Column 9, Line 67, replace "rabbits eyes" with --rabbit's eyes--.

Signed and Sealed this

Twelfth Day of June, 2007

JON W. DUDAS
*Director of the United States Patent and Trademark Office*